(12) United States Patent
Silvestrini et al.

(10) Patent No.: US 11,013,872 B2
(45) Date of Patent: May 25, 2021

(54) AEROSOL-GENERATING SYSTEM FOR GENERATING AND CONTROLLING THE QUANTITY OF NICOTINE SALT PARTICLES

(71) Applicant: PHILIP MORRIS PRODUCTS S.A., Neuchatel (CH)

(72) Inventors: Patrick Charles Silvestrini, Neuchatel (CH); Ihar Zinovik, Peseux (CH)

(73) Assignee: PHILIP MORRIS PRODUCTS S.A., Neuchatel (CH)

( * ) Notice: Subject to any disclaimer, the term of this patent is extended or adjusted under 35 U.S.C. 154(b) by 698 days.

(21) Appl. No.: 15/104,118

(22) PCT Filed: Dec. 12, 2014

(86) PCT No.: PCT/EP2014/077545
§ 371 (c)(1),
(2) Date: Jun. 13, 2016

(87) PCT Pub. No.: WO2015/091258
PCT Pub. Date: Jun. 25, 2015

(65) Prior Publication Data
US 2016/0309784 A1 Oct. 27, 2016

(30) Foreign Application Priority Data
Dec. 19, 2013 (EP) .................................. 13198390

(51) Int. Cl.
*A24F 40/50* (2020.01)
*A61M 15/06* (2006.01)
(Continued)

(52) U.S. Cl.
CPC ............. *A61M 15/06* (2013.01); *A24B 15/16* (2013.01); *A24F 40/30* (2020.01); *A24F 40/42* (2020.01);
(Continued)

(58) Field of Classification Search
CPC ........... A61M 15/0003; A61M 15/0066; A24F 47/008
See application file for complete search history.

(56) References Cited

U.S. PATENT DOCUMENTS 6,040,560 A 3/2000 Fleischhauer et al.
6,234,167 B1 * 5/2001 Cox .................. A61M 15/0003
128/200.14
(Continued)

FOREIGN PATENT DOCUMENTS

CN 101264333 A 9/2008
CN 102612361 A 7/2012
(Continued)

OTHER PUBLICATIONS

Office Action dated Aug. 17, 2017 in Kazakhstan patent application No. 2016/0632.1 (with English translation).
(Continued)

*Primary Examiner* — Michael J Felton
*Assistant Examiner* — Taryn Trace Willett
(74) *Attorney, Agent, or Firm* — Oblon, McClelland, Maier & Neustadt, L.L.P.

(57) ABSTRACT

There is provided an aerosol-generating system including an aerosol-generating device in cooperation with an aerosol-generating article. The aerosol-generating article includes a first compartment including a volatile liquid; and a second compartment including a delivery enhancing compound. The aerosol-generating device includes an outer housing configured to receive the aerosol-generating article; a power supply; a heater, configured to receive power from the power supply and arranged to heat the first compartment when the aerosol-generating article is received in the outer housing; an input, configured to receive an input from a user; and a controller, configured to control an amount of power supplied to the heater in dependence on a user input, such that
(Continued)

Figure 1A:
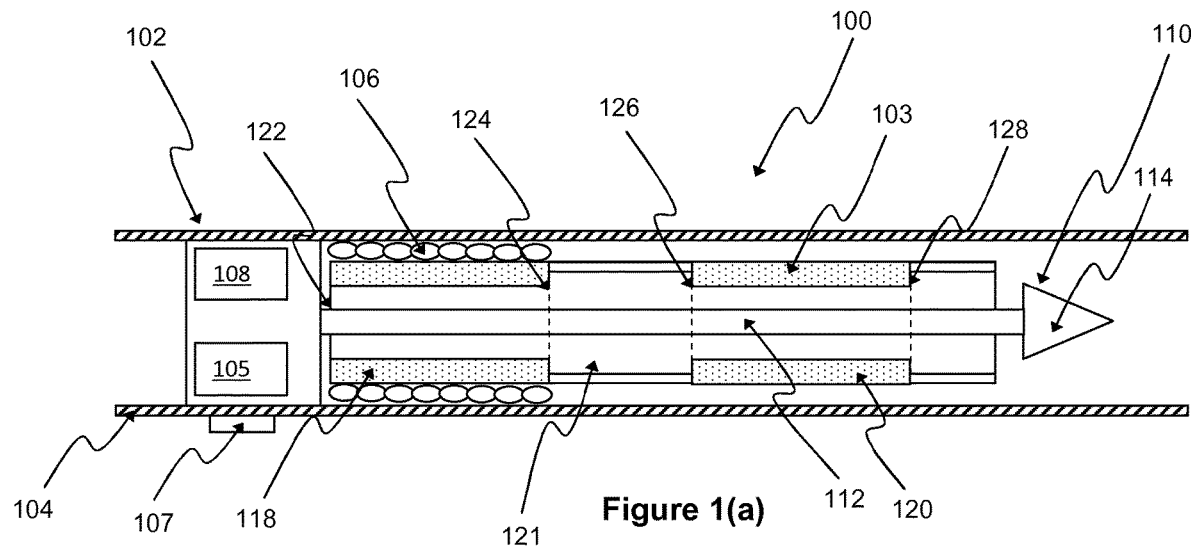

a quantity of volatile liquid aerosolised is determined by the user input.

12 Claims, 2 Drawing Sheets

(51) Int. Cl.
*A61M 11/04* (2006.01)
*A61M 15/00* (2006.01)
*A24F 40/60* (2020.01)
*A24F 40/57* (2020.01)
*A24F 40/48* (2020.01)
*A24F 40/42* (2020.01)
*A24F 40/30* (2020.01)
*A24B 15/16* (2020.01)
*H05B 1/02* (2006.01)
*A24F 40/10* (2020.01)

(52) U.S. Cl.
CPC .............. *A24F 40/48* (2020.01); *A24F 40/50* (2020.01); *A24F 40/57* (2020.01); *A24F 40/60* (2020.01); *A61M 11/042* (2014.02); *A61M 15/0003* (2014.02); *A61M 15/0021* (2014.02); *A61M 15/0033* (2014.02); *A61M 15/0066* (2014.02); *H05B 1/0244* (2013.01); *A24F 40/10* (2020.01); *A61M 15/004* (2014.02); *A61M 2205/3368* (2013.01); *A61M 2205/3653* (2013.01); *A61M 2205/505* (2013.01); *A61M 2205/8206* (2013.01)

(56) References Cited

U.S. PATENT DOCUMENTS

| | | | | |
|---|---|---|---|---|
| 6,543,443 | B1* | 4/2003 | Klimowicz | A61M 15/0085 128/200.14 |
| 8,349,251 | B2* | 1/2013 | Woo | A01M 1/2033 239/34 |
| 9,974,743 | B2* | 5/2018 | Rose | A61K 9/12 |
| 2004/0033171 | A1* | 2/2004 | Kvietok | A01M 1/2033 422/123 |
| 2005/0224075 | A1* | 10/2005 | Childers | A61M 15/0065 128/200.14 |
| 2005/0251289 | A1* | 11/2005 | Bonney | A61M 15/00 700/244 |
| 2005/0263618 | A1* | 12/2005 | Spallek | A61M 15/0065 239/433 |
| 2006/0054165 | A1* | 3/2006 | Hughes | A61M 15/009 128/200.14 |
| 2007/0068523 | A1* | 3/2007 | Fishman | A61M 16/0051 128/203.12 |
| 2007/0240712 | A1* | 10/2007 | Fleming | A61M 15/0028 128/203.15 |
| 2008/0092912 | A1* | 4/2008 | Robinson | A24F 47/008 131/200 |
| 2008/0241255 | A1 | 10/2008 | Rose et al. | |
| 2010/0200006 | A1 | 8/2010 | Robinson et al. | |
| 2011/0220106 | A1 | 9/2011 | Ganem et al. | |
| 2012/0048266 | A1* | 3/2012 | Alelov | A61M 11/005 128/202.21 |
| 2012/0055467 | A1* | 3/2012 | Brambilla | A61M 15/009 128/200.21 |
| 2012/0060853 | A1 | 3/2012 | Robinson et al. | |
| 2012/0227752 | A1 | 9/2012 | Alelov | |
| 2012/0255567 | A1* | 10/2012 | Rose | A61K 9/12 131/273 |
| 2014/0014126 | A1* | 1/2014 | Peleg | A24F 47/008 131/329 |
| 2014/0060556 | A1* | 3/2014 | Liu | A24F 47/008 131/329 |
| 2014/0224245 | A1 | 8/2014 | Alelov | |
| 2014/0246033 | A1* | 9/2014 | Daehne | A24F 47/002 131/329 |
| 2014/0261488 | A1* | 9/2014 | Tucker | A24F 47/008 131/328 |
| 2014/0299124 | A1* | 10/2014 | Lu | A61M 11/06 128/200.19 |
| 2015/0047662 | A1* | 2/2015 | Hopps | A24F 47/008 131/329 |
| 2015/0053217 | A1* | 2/2015 | Steingraber | A24F 47/008 131/329 |
| 2016/0089508 | A1* | 3/2016 | Smith | A61M 15/06 128/200.16 |
| 2016/0219938 | A1* | 8/2016 | Mamoun | G05B 15/02 |
| 2018/0043114 | A1* | 2/2018 | Bowen | A61M 15/06 |

FOREIGN PATENT DOCUMENTS

| | | |
|---|---|---|
| CN | 103404969 A | 11/2013 |
| EP | 1 867 357 A1 | 12/2007 |
| JP | 2010-506594 | 3/2010 |
| JP | 2012-249854 | 12/2012 |
| JP | 2013-505240 | 2/2013 |
| KZ | 26743 B | 3/2013 |
| KZ | 27104 B | 6/2013 |
| WO | 2008/121610 A1 | 10/2008 |
| WO | 2013/152873 A1 | 10/2013 |
| WO | WO 2014/102091 A1 | 7/2014 |

OTHER PUBLICATIONS

International Search Report and Written Opinion dated Feb. 18, 2015 in PCT/EP2014/077545 Filed Dec. 12, 2014.
Combined Chinese Office Action and Search Report dated May 11, 2018 in corresponding Patent Application No. 201480065223.4 (with English Translation), 20 pages.
Japanese Office Action with English translation dated Dec. 20, 2018 in corresponding Japanese Patent Application No. 2016-533691, (19 pages).

* cited by examiner

AEROSOL-GENERATING SYSTEM FOR GENERATING AND CONTROLLING THE QUANTITY OF NICOTINE SALT PARTICLES

The present invention relates to an aerosol-generating system for delivering an aerosol to a user comprising an aerosol-generating device and an aerosol-generating article, and in particular to a smoking device for delivering aerosolised nicotine salt particles to a user in user controllable quantities. The invention further relates to an aerosol-generating device for receiving an aerosol-generating article.

Devices for delivering nicotine to a user comprising a nicotine source and a volatile delivery enhancing compound source are known. For instance, WO 2008/121610 A1 discloses a device in which nicotine and a volatile delivery enhancing compound are reacted with one another in the gas phase to form an aerosol of nicotine salt particles that is inhaled by the user. However, WO 2008/121610 A1 does not address how to enable the user to control the quantity of nicotine provided to the user during each puff.

In addition, electrically heated aerosol generating system are known which generate an aerosol by heating a substrate. One such system is disclosed in US 2008/0092912, where an electrical heater is configured to heat a tobacco containing substrate to generate an aerosol.

Other systems are known which are configured to deliver an aerosol to a user from two sources. For example, WO 2013/152873 A1 discloses an aerosol generating device comprising two reservoirs, each arranged to contain a separate aerosol producing composition, and mixing means to mix the two composition aerosols before delivering them to the user.

US 2012/0048266 discloses a similar system to that of WO 2013/152873 A1, where first and second substances are released to form an aerosol.

It is desirable to produce a controllable quantity of nicotine salt particles for delivery to a user. Consequently, it would be desirable to provide an aerosol-generating system of the type disclosed in WO 2008/121610 A1 that enables the control of the formation of an aerosol of nicotine salt particles for delivery to a user.

According to a first aspect of the present invention, there is provided an aerosol-generating system comprising an aerosol-generating device in cooperation with an aerosol-generating article. The aerosol-generating article comprising: a first compartment comprising a volatile liquid; and a second compartment comprising a delivery enhancing compound. The aerosol-generating device comprising: an outer housing adapted to receive the aerosol-generating article; a power supply; at least one heater, configured to receive power from the power supply and arranged to heat the first compartment when the aerosol-generating article is received in the outer housing; an input, configured to receive an input from a user; and a controller, configured to control the amount of power supplied to the heater in dependence on the user input, such that the quantity of volatile liquid aerosolised is determined by the user input.

As used herein, the term "aerosol-generating device" refers to an aerosol-generating device that interacts with an aerosol-generating article to generate an aerosol that is directly inhalable into a user's lungs thorough the user's mouth.

By providing an aerosol-generating system which enables a user to provide an input to determine the quantity of volatile liquid to be aerosolised, advantageously the user is provided with an improved user experience. In addition, a single type of aerosol-smoking article can be provided which meets the different requirements of different users, advantageously reducing manufacturing and supply costs.

The input is configured to receive a plurality of discrete inputs from a user, each discrete input corresponding to a respective discrete quantity of aerosolised volatile liquid required by the user. The input may be a plurality of switches, buttons or the like, each corresponding to a discrete input. The skilled person would understand that any other suitable type of input may be used, such as a display in conjunction with softkey buttons. The controller is configured to control the amount of power supplied to the heater by changing the duty cycle, each discrete input corresponding to a respective discrete duty cycle.

As used herein the term "duty cycle" refers to the relative wattage output of a power source compared to the maximum wattage output of that source. Thus, a 70% duty cycle indicates that the power source is delivering a wattage output that is 70% of the maximum wattage output that the power source can deliver.

The discrete duty cycles may include: between about 90% and about 100%; between about 80% and about 90%; and about 55% and about 65%. Although it will be understood that any other suitable duty cycle may be used to result in the required quantity of volatile liquid being aerosolised.

Each discrete duty cycle is preferably a steady-state portion of a respective discrete power profile. Each discrete power profile preferably comprises a plurality of duty cycles, including the steady-state duty cycle. The steady-state duty cycle is preferably the final duty cycle in a series of the plurality of duty cycles. The series of the plurality of duty cycles preferably includes a first duty cycle of between about 90% and about 100%. At least one of the plurality of power profiles preferably comprises a second duty cycle of between about 65% and about 75%.

In a preferred embodiment, the controller is preferably configured to control power to the heater using one of three power profiles. The first power profile preferably comprises one duty cycle of between about 90% and about 100%, and in a particularly preferred embodiment about 95%. The second power profile preferably comprises two consecutive duty cycles, the first duty cycle being between about 90% and about 100%, and the second duty cycle being between 80% and about 90%, and in a particularly preferred embodiment the first duty cycle being 95% and the second duty cycle being 85%. The third power profile preferably comprises three consecutive duty cycles, the first duty cycle being between about 90% and about 100%, the second duty cycle being between 65% and about 75%, and the third duty cycle being between about 55% and about 65%, and in a particularly preferred embodiment the first duty cycle being 95%, the second duty cycle being 70%, and the third duty cycle being 60%.

The quantity of volatile liquid aerosolised is dependent on the temperature of the compartment being heated, the temperature of the compartment being related to the power supplied to the heater.

The volatile liquid preferably comprises nicotine, and the quantity of nicotine aerosolised per puff of the user on the aerosol-generating device is controllable between about 50 micrograms and about 150 micrograms. Each smoking article preferably has sufficient volatile liquid to provide at least one usage event defined as 12 puffs. In a preferred embodiment, each aerosol-generating article preferably has sufficient volatile liquid to enable a plurality of usage events. As will be appreciated, reducing the quantity of volatile liquid aerosolised during each puff, enables more usage events per aerosol-generating article.

In an alternative embodiment, the input may be configured to receive a continuous range of inputs from a user, the range of inputs corresponding to a respective range of quantities of aerosolised volatile liquid. In this alternative embodiment, the controller is preferably configured to control the amount of power supplied to the heater by changing the duty cycle from between a minimum duty cycle of about 50% and a maximum duty cycle of about 100%. In this way, the user is provided with an aerosol-generating system which enables the quantity of volatile liquid aerosolised to be continuously varied.

The power supply is preferably a battery, and more preferably a rechargeable battery.

The at least one heater may be an electrically resistive heater. The heater may be a coil arranged on the internal surface of the cavity configured to receive the aerosol-generating article. The aerosol-generating device may comprise one, two, three, four, five, six or more heaters.

In one embodiment, the aerosol-generating device further comprises at least one further heater configured to receive power from the power supply and arranged to heat the second compartment when the aerosol-generating article is received in the outer housing. In this embodiment, the controller is further configured to control the amount of power supplied to the at least one further heater, such that the quantity of delivery enhancing compound aerosolised is proportional to the quantity of volatile liquid aerosolised.

The second compartment is preferably heated to a lower temperature than the first compartment, because, as described herein, the vapour pressure of the delivery enhancing compound may be lower than the vapour pressure of the volatile liquid nicotine.

Preferably, the controller is further configured to control the amount of power supplied to the at least one further heater by changing the duty cycle. The duty cycle for the at least one heater, for the first compartment, being different to the duty cycle for the at least one further heater, for the second compartment. The duty cycle for the at least one heater and the duty cycle for the at least one further heater may be independent.

Preferably, the duty cycle for the at least one heater is greater than the duty cycle for the at least one further heater. As a result, the temperature of the first compartment is preferably higher than the temperature of the second compartment.

The duty cycle for the at least one further heater may be between about 0% and about 45%, more preferably between about 1% and about 30%, and most preferably between about 3% and 20%.

In a preferred embodiment, the ratio of the duty cycle for the at least one heater to the duty cycle for the at least one further heater is between about 1.5:1 to about 10:1, preferably 2:1 to 8:1, most preferably between about 3:1 to about 6:1.

In preferred embodiments, the at least one heater is an external heater comprising an external heating element, and where present the at least one further heater is an external heater comprising an external heating element.

As used herein, the terms "external heater" and "external heating element" refer to a heater and heater element, respectively, that are positioned externally to an aerosol-generating article received in the housing of the aerosol-generating device.

As will be appreciated, providing different duty cycles to the at least one heater and the at least one further heater, enables differential heating of the delivery enhancing compound and the volatile liquid of the aerosol-generating article. This allows precise control of the amount of volatile delivery enhancing compound vapour and volatile liquid vapour released from the first compartment and second compartment respectively. This advantageously enables the vapour concentrations of the volatile delivery enhancing compound and the volatile liquid to be controlled and balanced proportionally to yield an efficient reaction stoichiometry. This advantageously improves the efficiency of the formation of an aerosol and the consistency of the volatile liquid delivery to a user. It also advantageously reduces the delivery of unreacted delivery enhancing compound vapour and unreacted volatile liquid vapour to a user.

The aerosol-generating article may further comprise an insulating element between the first compartment and the second compartment. Providing an insulating element between the first compartment and the second compartment enables the temperature of the second compartment to be substantially independent of the temperature of the first compartment.

The first compartment and the second compartment of the aerosol-generating article are preferably sealed. A first end of the first compartment is preferably sealed by a frangible barrier, an interface between a second end of the first compartment and a first end of the second compartment is preferably sealed by at least one frangible barrier, and a second end of the second compartment is preferably sealed by a frangible barrier. Each frangible barrier may be made from metal film, and more preferably from aluminium film.

The aerosol-generating article preferably further comprises at least one air inlet upstream of the first compartment, and at least one air outlet downstream of the second compartment, the at least one air inlet and the at least one air outlet being arranged to define an air flow pathway extending from the at least one air inlet to the at least one air outlet via the first compartment, and via the second compartment.

In such embodiments, the first compartment and the second compartment are arranged in series from air inlet to air outlet within the aerosol-generating system. That is, the first compartment is downstream of the air inlet, the second compartment is downstream of the first compartment and the air outlet is downstream of the second compartment. In use, a stream of air is drawn into the aerosol-generating system through the air inlet, downstream through the first compartment and the second compartment and out of the aerosol-generating system through the air outlet.

As used herein, the term "air inlet" is used to describe one or more apertures through which air may be drawn into the aerosol-generating system.

As used herein, the term "air outlet" is used to describe one or more aperture through which air may be drawn out of the aerosol-generating system.

The second compartment preferably comprises a tubular porous element having the delivery enhancing compound sorbed thereon. As used herein, by "sorbed" it is meant that the delivery enhancing compound is adsorbed on the surface of the tubular porous element, or absorbed in the tubular porous element, or both adsorbed on and absorbed in the tubular porous element.

The internal diameter of the tubular porous element is preferably between about 2 mm and about 5 mm, more preferably between about 2.5 mm and about 3.5 mm. In a preferred embodiment, the internal diameter of the tubular porous element is about 3 mm.

The tubular porous element preferably has a longitudinal length of between about 7.5 mm and about 15 mm, more preferably of between about 9 mm and about 11 mm, and in the preferred embodiment the tubular porous element has a longitudinal length of about 10 mm.

In a preferred embodiment the tubular porous element is a hollow cylinder. The hollow cylinder is preferably a right circular hollow cylinder.

The aerosol-generating device preferably further comprises an elongate piercing member for piercing the first compartment and the second compartment of the aerosol-generating article. The elongate piercing member comprises: a piercing portion adjacent a distal end of the elongate piercing member; and a shaft portion. The piercing portion preferably has a maximum diameter greater than the diameter of the shaft portion. The piercing member is preferably positioned within the outer housing along the central longitudinal axis of the aerosol-generating device.

The maximum diameter of the piercing portion is preferably between about 105% and about 125% of the diameter of the shaft portion. More preferably, the maximum diameter of the piercing portion is between about 110% and about 120% of the diameter of the shaft portion. In a preferred embodiment, the maximum diameter of the piercing portion is about 120% of the diameter of the shaft portion.

The piercing portion preferably has a maximum diameter of between about 75% and about 100% of the internal diameter of the hollow cylinder.

In a preferred embodiment the piercing portion is conical. However, it should be understood that the piercing portion may be of any shape suitable for piercing the compartments of the aerosol-generating article. Where the piercing portion is conical, the maximum diameter of the piercing portion corresponds to the diameter of the base circle of the cone.

The maximum diameter of the piercing portion is preferably between about 1.5 mm and about 5 mm, more preferably between about 1.75 mm and about 3.5 mm. In a preferred embodiment, the piercing portion has a maximum diameter of about 3 mm.

As used herein, the terms 'upstream', 'downstream' and 'distal' and 'proximal' are used to describe the relative positions of components, or portions of components, of aerosol-generating articles, aerosol-generating devices and aerosol-generating systems according to the invention in relation to the direction of air drawn through the aerosol-generating articles, aerosol-generating devices and aerosol-generating systems during use thereof. It will be understood that the terms 'distal' and 'proximal', when used to describe the relative positions of components of the elongate piercing member, are used such that the piercing portion is at the distal, 'free', end and the obstructing portion is at the proximal, 'fixed', end which is connected to the device.

The upstream and downstream ends of the aerosol-generating article are defined with respect to the airflow when a user draws on the proximal or mouth end of the aerosol-generating article. Air is drawn into the aerosol-generating article at the distal or upstream end, passes downstream through the aerosol-generating articles and exits the aerosol-generating article at the proximal or downstream end.

As used herein, the term "longitudinal" is used to describe the direction between the downstream or proximal end and the opposed upstream or distal end of the aerosol-generating article or aerosol-generating device and the term "transverse" is used to describe the direction perpendicular to the longitudinal direction.

The first compartment is preferably a hollow cylinder, and the piercing portion preferably has a maximum diameter of between about 50% and about 75% of the internal diameter of the first compartment.

The first compartment preferably has an internal diameter of between about 4 mm and about 8 mm, more preferably between about 5 mm and about 7 mm. In a preferred embodiment the first compartment has an internal diameter of about 6.5 mm.

The first compartment preferably has a longitudinal length of between about 5 mm and about 50 mm, more preferably between about 5 mm and about 20 mm. In a preferred embodiment the second compartment has a longitudinal length of about 10 mm.

The longitudinal length of the elongate piercing member is preferably greater than the total longitudinal length of the first compartment and the second compartment. Providing a piercing member having such a length enables the first compartment and the second compartment of the aerosol-generating article to be pierced. This enables air to flow through the first and second compartments when the aerosol-generating system is in use.

The shaft of the piercing member preferably has a diameter of between about 1 mm and about 3 mm, more preferably between about 1.5 mm and about 2.5 mm. In a preferred embodiment the shaft has a diameter of about 2 mm. The shaft of the piercing member is provided with a smaller diameter than the maximum diameter of the piercing portion so that, in use, air can flow around the shaft and through the holes formed in the first and second compartments by the piercing portion.

The volume of the first compartment and the second compartment may be the same or different. In a preferred embodiment, the volume of the second compartment is greater than the volume of the first compartment.

The aerosol-generating article preferably further comprises at least one further element. The aerosol-generating article may further comprise one, two, three, four, five or more further elements. The further element may be any of: a filter element; a third compartment; an aerosol forming chamber; and a hollow tube. In a preferred embodiment the further element comprises a mouthpiece. The mouthpiece may be sealed at the proximal end of the aerosol-generating article.

The mouthpiece may comprise any suitable material or combination of materials. Examples of suitable materials include thermoplastics that are suitable for food or pharmaceutical applications, for example polypropylene, polyetheretherketone (PEEK) and polyethylene.

In a preferred embodiment the outer housing of the aerosol-generating device comprises a cavity configured to receive the aerosol-generating article. Preferably, the cavity has a longitudinal length greater than the longitudinal length of the elongate piercing member. In this way, the piercing portion of the piercing member is not exposed, or accessible by the user. Preferably, the cavity of the aerosol-generating device is substantially cylindrical. The cavity of the aerosol-generating device may have a transverse cross-section of any suitable shape. For example, the cavity may be of substantially circular, elliptical, triangular, square, rhomboidal, trapezoidal, pentagonal, hexagonal or octagonal transverse cross-section.

Preferably, the cavity of the aerosol-generating device has a transverse cross-section of substantially the same shape as the transverse cross-section of the aerosol-generating article to be received in the cavity.

The overall dimensions of the aerosol-generating system may be similar to a conventional smoking article such as a cigarette, a cigar a cigarillo or any other such smoking article.

In use, the user inserts the aerosol-generating article into the outer housing of the aerosol-generating device. The user then chooses the required quantity of volatile liquid to be aerosolised during each puff, and inputs that choice into the aerosol-generating device. In dependence on the input, the controller provides power from the power supply to the heater in accordance with one of a plurality, preferably three, power profiles. The user then draws on the proximal end of the aerosol-generating article causing air to flow along the air flow pathway, entraining volatile liquid vapour generated in the first compartment by the heater, the rate at which the liquid is vaporised being dependent on the power profile used, and entraining delivery enhancing compound vapour from the delivery enhancing compound sorbed on the porous tubular element of the second compartment. An aerosol is generated by the delivery enhancing compound vapour reacting with the volatile liquid vapour in the gas phase. The generation of the aerosol is described in further detail below.

According to a further aspect of the present invention, there is provided an aerosol-generating device for an aerosol-generating system as described herein. The aerosol generating device comprises: an outer housing, adapted to receive an aerosol-generating article comprising a first compartment comprising a volatile liquid, and a second compartment comprising a delivery enhancing compound; a power supply; a heater, configured to receive power from the power supply and arranged to heat the first compartment when an aerosol-generating article is received in the outer housing; an input, configured to receive a plurality of discrete inputs from a user; and a controller, configured to control the amount of power supplied to the heater by changing the duty cycle in dependence on the user input, each discrete input from the user corresponding to a respective discrete duty cycle, such that each discrete input corresponds to a respective discrete quantity of aerosolised volatile liquid required by the user. As used herein, the term "aerosol-generating device" refers to an aerosol-generating device that interacts with an aerosol-generating article to generate an aerosol that is directly inhalable into a user's lungs thorough the user's mouth.

The volatile liquid of the first compartment may be a medicament. Preferably, the medicament has a melting point below about 150 degrees Celsius.

Alternatively or in addition, preferably the medicament has a boiling point below about 300 degrees Celsius.

In certain preferred embodiments, the medicament comprises one or more aliphatic or aromatic, saturated or unsaturated nitrogenous bases (nitrogen containing alkaline compounds) in which a nitrogen atom is present in a heterocyclic ring or in an acyclic chain (substitution).

The medicament may comprise one or more compounds selected from the group consisting of: nicotine; 7-Hydroxymitragynine; Arecoline; Atropine; Bupropion; Cathine (D-norpseudoephedrine); Chlorpheneramine; Dibucaine; Dimemorphan, Dimethyltryptamine, Diphenhydramine, Ephedrine, Hordenine, Hyoscyamine, Isoarecoline, Levorphanol, Lobeline, Mesembrine, Mitragynine, Muscatine, Procaine, Pseudo ephedrine, Pyrilamine, Raclopride, Ritodrine, Scopolamine, Sparteine (Lupinidine) and Ticlopidine; tobacco smoke constituents, such as 1,2,3,4 Tetrahydroisoquinolines, Anabasine, Anatabine, Cotinine, Myosmine, Nicotrine, Norcotinine, and Nornicotine; anti-asthmatic drugs, such as Orciprenaline, Propranolol and Terbutaline; anti-angina drugs, such as Nicorandil, Oxprenolol and Verapamil; anti-arrhythmic drugs, such as Lidocaine; nicotinic agonists, such as Epibatidine, 5-(2R)-azetidinylmethoxy)-2-chloropyridine (ABT-594), (S)-3-methyl-5-(1-methyl-2-pyrrolidinyl)isoxazole (ABT 418) and (±)-2-(3-Pyridinyl)-1-azabicyclo[2.2.2]octane (RJR-2429); nicotinic antagonists, such as Methyllycacotinine and Mecamylamine; acetyl cholinesterase inhibitors, such as Galantamine, Pyridostigmine, Physostigmine and Tacrine; and MAO-inhibitors, such as Methoxy-N,N-dimethyltryptamine, 5-methoxy-a-methyltryptamine, Alpha-methyltryptamine, Iproclozide, Iproniazide, Isocarboxazide, Linezolid, Meclobemide, N,N-Dimethyltryptamine, Phenelzine, Phenyl ethylamine, Toloxatone, Tranylcypromine and Tryptamine.

Referring to the aerosol-generating article, in a preferred embodiment, the first compartment comprises a source of nicotine. As such, the volatile liquid within the first compartment preferably comprises one or more of nicotine, nicotine base, a nicotine salt, or a nicotine derivative.

The source of nicotine may comprise natural nicotine or synthetic nicotine. The source of nicotine may comprise nicotine base, a nicotine salt, such as nicotine-HCl, nicotine-bitartrate, or nicotine-ditartrate, or a combination thereof.

The source of nicotine may further comprise an electrolyte forming compound. The electrolyte forming compound may be selected from the group consisting of alkali metal hydroxides, alkali metal oxides, alkaline earth metal oxides, sodium hydroxide (NaOH), calcium hydroxide (Ca(OH)$_2$), potassium hydroxide (KOH) and combinations thereof.

Alternatively or in addition, the source of nicotine may further comprise other components including, but not limited to, natural flavours, artificial flavours and antioxidants.

Preferably, the first compartment comprises a liquid nicotine formulation. Preferably, the first compartment is configured to hold between about 5 microlitres and about 50 microlitres of the liquid nicotine formulation, more preferably about 10 microlitres of the liquid nicotine formulation.

The liquid nicotine formulation may comprise pure nicotine, a solution of nicotine in an aqueous or non-aqueous solvent or a liquid tobacco extract.

The liquid nicotine solution may comprise an aqueous solution of nicotine base, a nicotine salt, such as nicotine-HCl, nicotine-bitartrate, or nicotine-ditartrate and an electrolyte forming compound.

The first compartment may comprise a sorption element and nicotine sorbed on the sorption element. In a preferred embodiment, the first compartment comprises a volatile liquid nicotine source.

In a preferred embodiment, the aerosol-generating article further comprises an aerosol forming chamber in fluid communication with the first compartment and the second compartment. In use, in a preferred embodiment the nicotine reacts with the acid or ammonium chloride in the gas phase in the aerosol forming chamber to form aerosolised nicotine salt particles.

Alternatively, the delivery enhancing compound vapour may react with the nicotine vapour in the second compartment. In such embodiments the aerosol-generating article may further comprise a third compartment downstream of the second compartment and the delivery enhancing compound vapour may alternatively or in addition react with the nicotine vapour in the third compartment to form an aerosol.

The second compartment of the aerosol-generating article preferably comprises a volatile delivery enhancing compound. As used herein, by "volatile" it is meant the delivery enhancing compound has a vapour pressure of at least about 20 Pa. Unless otherwise stated, all vapour pressures referred to herein are vapour pressures at 25° C. measured in accordance with ASTM E1194-07.

Preferably, the volatile delivery enhancing compound has a vapour pressure of at least about 50 Pa, more preferably at least about 75 Pa, most preferably at least 100 Pa at 25° C.

Preferably, the volatile delivery enhancing compound has a vapour pressure of less than or equal to about 400 Pa, more preferably less than or equal to about 300 Pa, even more preferably less than or equal to about 275 Pa, most preferably less than or equal to about 250 Pa at 25° C.

In certain embodiments, the volatile delivery enhancing compound may have a vapour pressure of between about 20 Pa and about 400 Pa, more preferably between about 20 Pa and about 300 Pa, even more preferably between about 20 Pa and about 275 Pa, most preferably between about 20 Pa and about 250 Pa at 25° C.

In other embodiments, the volatile delivery enhancing compound may have a vapour pressure of between about 50 Pa and about 400 Pa, more preferably between about 50 Pa and about 300 Pa, even more preferably between about 50 Pa and about 275 Pa, most preferably between about 50 Pa and about 250 Pa at 25° C.

In further embodiments, the volatile delivery enhancing compound may have a vapour pressure of between about 75 Pa and about 400 Pa, more preferably between about 75 Pa and about 300 Pa, even more preferably between about 75 Pa and about 275 Pa, most preferably between about 75 Pa and about 250 Pa at 25° C.

In yet further embodiments, the volatile delivery enhancing compound may have a vapour pressure of between about 100 Pa and about 400 Pa, more preferably between about 100 Pa and about 300 Pa, even more preferably between about 100 Pa and about 275 Pa, most preferably between about 100 Pa and about 250 Pa at 25° C.

The volatile delivery enhancing compound may comprise a single compound. Alternatively, the volatile delivery enhancing compound may comprise two or more different compounds.

Where the volatile delivery enhancing compound comprises two or more different compounds, the two or more different compounds in combination have a vapour pressure of at least about 20 Pa at 25° C.

Preferably, the volatile delivery enhancing compound is a volatile liquid.

The volatile delivery enhancing compound may comprise a mixture of two or more different liquid compounds.

The volatile delivery enhancing compound may comprise an aqueous solution of one or more compounds. Alternatively the volatile delivery enhancing compound may comprise a non-aqueous solution of one or more compounds.

The volatile delivery enhancing compound may comprise two or more different volatile compounds. For example, the volatile delivery enhancing compound may comprise a mixture of two or more different volatile liquid compounds.

Alternatively, the volatile delivery enhancing compound may one or more non-volatile compounds and one or more volatile compounds. For example, the volatile delivery enhancing compound may comprise a solution of one or more non-volatile compounds in a volatile solvent or a mixture of one or more non-volatile liquid compounds and one or more volatile liquid compounds.

The delivery enhancing compound preferably comprises an acid or ammonium chloride. Preferably, the delivery enhancing compound comprises an acid. More preferably, the delivery enhancing compound comprises an acid having a vapour pressure of at least about 5 Pa at 20° C. Preferably, the acid has a greater vapour pressure than nicotine at 20° C.

The delivery enhancing compound may comprise an organic acid or an inorganic acid. Preferably, the delivery enhancing compound comprises an organic acid. More preferably, the delivery enhancing compound comprises a carboxylic acid. Most preferably, the delivery enhancing compound comprises an alpha-keto or 2-oxo acid.

In a preferred embodiment, the delivery enhancing compound comprises an acid selected from the group consisting of 3-methyl-2-oxovaleric acid, pyruvic acid, 2-oxovaleric acid, 4-methyl-2-oxovaleric acid, 3-methyl-2-oxobutanoic acid, 2-oxooctanoic acid and combinations thereof. In a particularly preferred embodiment, the delivery enhancing compound comprises pyruvic acid.

Were present, the tubular porous element is preferably a sorption element with an acid or ammonium chloride sorbed thereon. The tubular porous element may be formed from any suitable material or combination of materials. For example, the sorption element may comprise one or more of glass, stainless steel, aluminium, polyethylene (PE), polypropylene, polyethylene terephthalate (PET), polybutylene terephthalate (PBT), polytetrafluoroethylene (PTFE), expanded polytetrafluoroethylene (ePTFE), and BAREX®.

Where present, the tubular porous element may comprise one or more porous materials selected from the group consisting of porous plastic materials, porous polymer fibres and porous glass fibres. The one or more porous materials may or may not be capillary materials and are preferably inert with respect to the acid or ammonium chloride. The particular preferred porous material or materials will depend on the physical properties of the acid or ammonium chloride. The one or more porous materials may have any suitable porosity so as to be used with different acids having different physical properties.

Suitable porous fibrous materials include, but are not limited to: cellulose cotton fibres, cellulose acetate fibres and bonded polyolefin fibres, such as a mixture of polypropylene and polyethylene fibres.

The tubular porous element may have any suitable size and shape.

The size, shape and composition of the tubular porous element may be chosen to allow a desired amount of volatile delivery enhancing compound to be sorbed on the tubular porous element.

In a preferred embodiment, between about 10 µl and about 100 µl, more preferably between about 15 µl and about 50 µl, most preferably between about 15 µl and about 25 µl of the volatile delivery enhancing compound is sorbed on the tubular porous element.

The tubular porous element advantageously acts as a reservoir for the delivery enhancing compound.

The invention allows a cost effective, compact and easy to use aerosol-generating system to be provided. Furthermore, by using an acid or ammonium chloride as a delivery enhancing agent in aerosol-generating articles according to the invention, the pharmacokinetic rate of the nicotine may be advantageously increased.

It will be understood that the aerosol-generating system may also be regarded as an aerosol delivery system. That is to say, the aerosol-generating system provides means for the volatile liquid, such as a nicotine formulation, and the delivery enhancing compound, such as a pyruvic acid, to mix and generate an aerosol but does not actively generate the aerosol. In the embodiment where the aerosol-generating article comprises a third compartment, the third compartment is preferably downstream of the second compartment. Where the article comprises an aerosol forming chamber, the third compartment is preferably downstream of the aerosol forming chamber. The third compartment may comprise a flavour source. Alternatively or in addition, the third component may comprise a filtration material capable of removing at least a portion of any unreacted acid or ammonium chloride mixed with aerosolised nicotine salt particles drawn through the third compartment. The filtration material may comprise a sorbent, such as activated carbon. As will be appreciated, any number of additional compartments may be provided as desired. For example, the article may comprise a third compartment comprising a filter material and a fourth compartment downstream of the third compartment comprising a flavour source.

Preferably, the article comprises an opaque outer housing. This advantageously reduces the risk of degradation of the acid or ammonium chloride and nicotine formulation due to exposure to light.

Preferably, the aerosol-generating article is not refillable. Thus, when the nicotine formulation in the first compartment of the aerosol-generating article has been used up, the aerosol-generating article is replaced.

In certain embodiments, the device as well as the aerosol-generating article may be disposable.

Advantageously, all elements of the device which are potentially in contact with the acid or ammonium chloride or the source of nicotine are changed when the aerosol-generating article is replaced. This avoids any cross-contamination in the device between different mouthpieces and different aerosol-generating articles, for example aerosol-generating articles comprising different acids or sources of nicotine.

The nicotine formulation in the first compartment may be advantageously protected from exposure to oxygen (because oxygen cannot generally pass through the barrier of the first compartment until it is pierced by the piercing member) and in some embodiments light, so that the risk of degradation of the nicotine formulation is significantly reduced. Therefore, a high level of hygiene can be maintained.

The aerosol-generating article is preferably substantially cylindrical in shape. The aerosol-generating article may have a transverse cross-section of any suitable shape. Preferably, the aerosol-generating article is of substantially circular transverse cross-section or of substantially elliptical transverse cross-section. More preferably, the aerosol-generating article is of substantially circular transverse cross-section.

Preferably, the aerosol generating article has a transverse cross-section substantially the same shape as the cavity of the aerosol-generating device.

A housing of the aerosol-generating article may simulate the shape and dimensions of a tobacco smoking article, such as a cigarette, a cigar, a cigarillo or a pipe, or a cigarette pack. In a preferred embodiment, the housing simulates the shape and dimensions of a cigarette.

The aerosol-generating device and aerosol-generating article may be arranged to releasably lock together when engaged.

The outer housing of the device may be formed from any suitable material or combination of materials. Examples of suitable materials include, but are not limited to, metals, alloys, plastics or composite materials containing one or more of those materials. Preferably, the outer housing is light and non-brittle.

The aerosol-generating system and device are preferably portable. The aerosol-generating system may have a size and shape comparable to a conventional smoking article, such as a cigar or cigarette.

Any feature in one aspect of the invention may be applied to other aspects of the invention, in any appropriate combination. In particular, method aspects may be applied to apparatus aspects, and vice versa. Furthermore, any, some and/or all features in one aspect can be applied to any, some and/or all features in any other aspect, in any appropriate combination.

It should also be appreciated that particular combinations of the various features described and defined in any aspects of the invention can be implemented and/or supplied and/or used independently.

The invention will be further described, by way of example only, with reference to the accompanying drawings in which:

FIG. 1(*a*) shows a schematic representation of an aerosol-generating system according to the present invention;

FIG. 1(*b*) shows a schematic representation of an alternative aerosol-generating system to the present invention;

FIG. 2 shows a graph of a set of three power profiles used to apply power to the heater in an aerosol-generating system according to the invention; and FIG. 3 shows a graph of a set of three temperature profiles of the first compartment of an aerosol-generating system corresponding to the power profiles shown in FIG. 2.

FIG. 1(*a*) shows a schematic representation of an aerosol-generating system 100. The system 100 comprises an aerosol-generating device 102 and an aerosol-generating article 103. The aerosol-generating device comprises an outer housing 104, having an elongate cylindrical shape, for housing a power supply 105, an electrical heater 106, an input 107, control electronics 108, and a piercing member 110. The piercing member comprises an elongate shaft portion 112 and a piercing portion 114. The housing 104 has an elongate cylindrical cavity configured to receive the aerosol-generating article 103. The longitudinal length of the cavity is less than the length of the article 103 such that the proximal, or downstream, end of the article 103 protrudes from the cavity. The piercing member 110 is positioned centrally within the cavity of the aerosol-generating device and extends along the longitudinal axis of the cavity.

Air inlets (not shown) are provided at the distal, upstream, end of the aerosol-generating device 102. Air outlets (not shown) are provided at the proximal, downstream, end of the aerosol-generating article 103.

The aerosol-generating article 103 also has an elongate cylindrical shape and comprises a first compartment 118 comprising a volatile liquid nicotine source, and a second compartment 120 comprising a volatile delivery enhancing compound source. The first compartment comprises a tubular porous element, upon which is sorbed the volatile liquid nicotine source. The second compartment also comprises a tubular porous element upon which is sorbed the volatile delivery enhancing compound source.

The first compartment 118 and the second compartment 120 are arranged in series and are spaced apart along the longitudinal axis of the aerosol-generating article. An insulating portion 121 is provided between the first compartment and the second compartment. The first compartment 118 is positioned at the distal, or upstream, end of the aerosol-generating article 103. The second compartment 120 is positioned downstream of the first compartment. A further element (not shown) in the form of a mouthpiece or the like may be provided at the downstream end of the second compartment.

The upstream and downstream ends of the first compartment 118 and the second compartment 120 of the aerosol-generating article 103 are sealed by frangible barriers 122, 124 and 126, 128 respectively. The frangible barriers are made from metal film, such as aluminium.

In use, as the aerosol-generating article 103 is inserted into the cavity of the aerosol-generating device 102 the piercing member 110 is inserted into the aerosol-generating article 103 and pierces the frangible barriers 122, 124, 126 and 128 at the upstream and downstream ends of the first compartment 118 and second compartment 120 of the aerosol-generating article 103. This allows a user to draw air into the aerosol-generating article through the air inlets at the distal, upstream, end thereof, downstream through the first compartment, and the second compartment and out of the article through the air outlets at the proximal, downstream, end thereof. The air flow pathway further extends about the shaft of the piercing member via the hole made in the frangible barrier 128 at the proximal, downstream end of the second compartment, and then about the piercing portion 114. By providing a shaft having a smaller diameter than the maximum diameter of the piercing portion, the air flow pathway is enabled to extend around the shaft in the region of the frangible barrier.

Nicotine vapour is released from the volatile liquid nicotine source in the first compartment 118 into the air stream drawn through the aerosol-generating article 103. Delivery enhancing compound vapour, which in the preferred embodiment contains pyruvic acid, is released from the delivery enhancing compound sorbed on the tubular porous element of the second compartment 122 into the air stream drawn through the aerosol-generating article 103. The delivery enhancing compound vapour reacts with the nicotine vapour in the gas phase to form an aerosol, which is delivered to the user through the proximal, downstream, end of the aerosol-generating article 103.

To control the quantity of nicotine vapour released from the volatile liquid nicotine source in the first compartment, the control circuitry provides a controlled power profile to the heater. The user inputs the required quantity via the input 107, and thus the controller applies the corresponding power profile. In general, each power profile comprises a steady-state duty cycle which varies in accordance with the quantity of nicotine required.

Figure 1B:
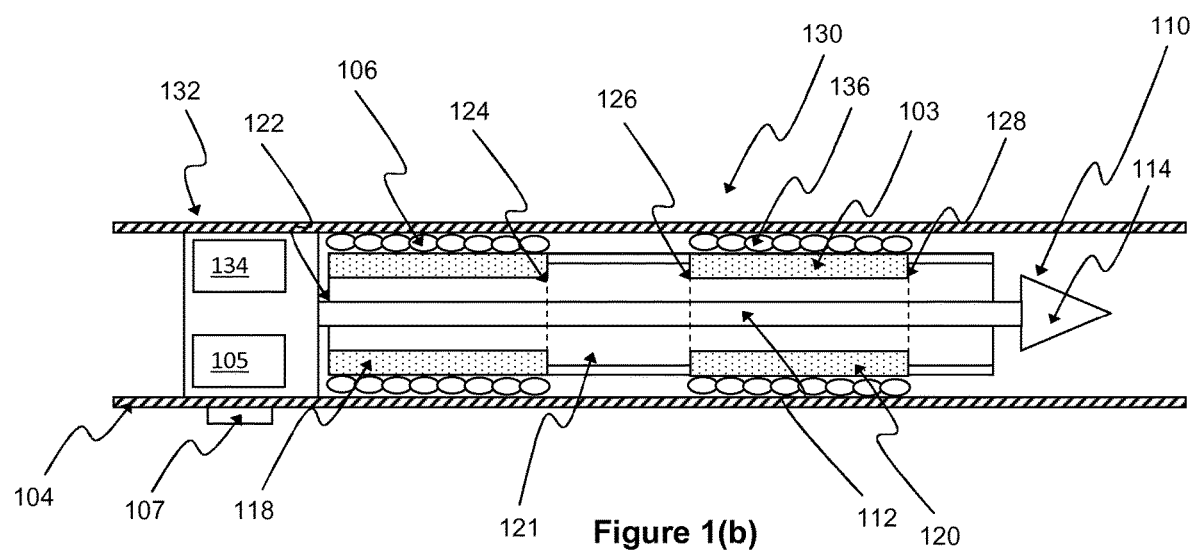

FIG. 1(b) shows a schematic representation of an alternative aerosol-generating system 130. The system 130 is similar to the system 100 shown in FIG. 1(a) and like reference numerals refer to like components. The system 130 comprises an aerosol-generating device 132 and an aerosol-generating article 103. The aerosol-generating device comprises an outer housing 104, for housing a power supply 105, an electrical heater 106, an input 107, control electronics 134, and a piercing member 110. The device 132 further comprises a second heater 136 configured to heat the second compartment of the aerosol-generating article 103.

Similarly to the system shown in FIG. 1(a), to control the quantity of nicotine vapour released from the volatile liquid nicotine source in the first compartment, the control circuitry 134 provides a controlled power profile to the heater 106. The user inputs the required quantity via the input 107, and thus the controller applies the corresponding power profile. In general, each power profile comprises a steady-state duty cycle which varies in accordance with the quantity of nicotine required. In addition, the control circuitry 134 provides a controlled power profile to the second heater 136 to heat the second compartment to a different temperature to that of the first compartment. In general, the controller is configured to provide less power to the second heater as compared to the first heater, and hence provides a lower duty cycle to the second heater as compared to the duty cycle provided to the first heater.

Figure 2:
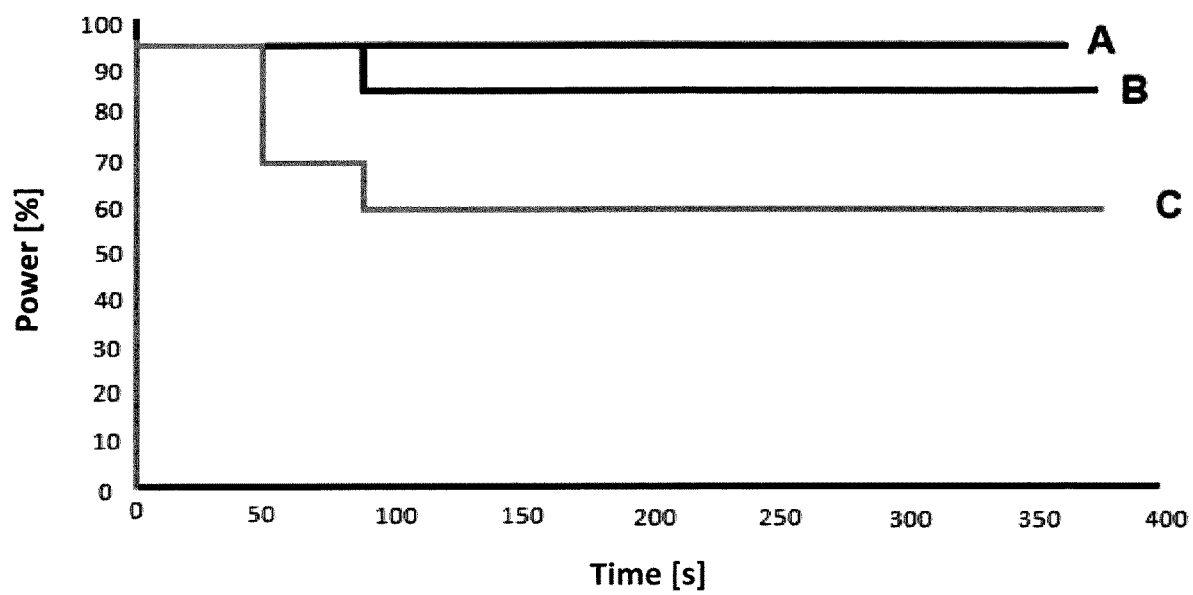

FIG. 2 shows a set of three example power profiles. A first profile, A, has a single steady-state duty cycle of 95% The second profile, B, comprises two duty cycles, a first of 95%, and a second of 85%. The third profile, C, comprises three duty cycles, a first of 95%, a second of 70% and a third of 60%. The power profiles are designed to increase the temperature of the first compartment to a minimum operating temperature in as short amount of time as possible. The third power profile is configured to substantially hold the temperature of the first compartment at this minimum operating temperature. The second power profile is configured to increase the temperature further, and the first power profile is configured to increase the temperature to a maximum operating temperature. As will be appreciated, the amount of nicotine vapourised increases with increasing operating temperature.

Figure 3:
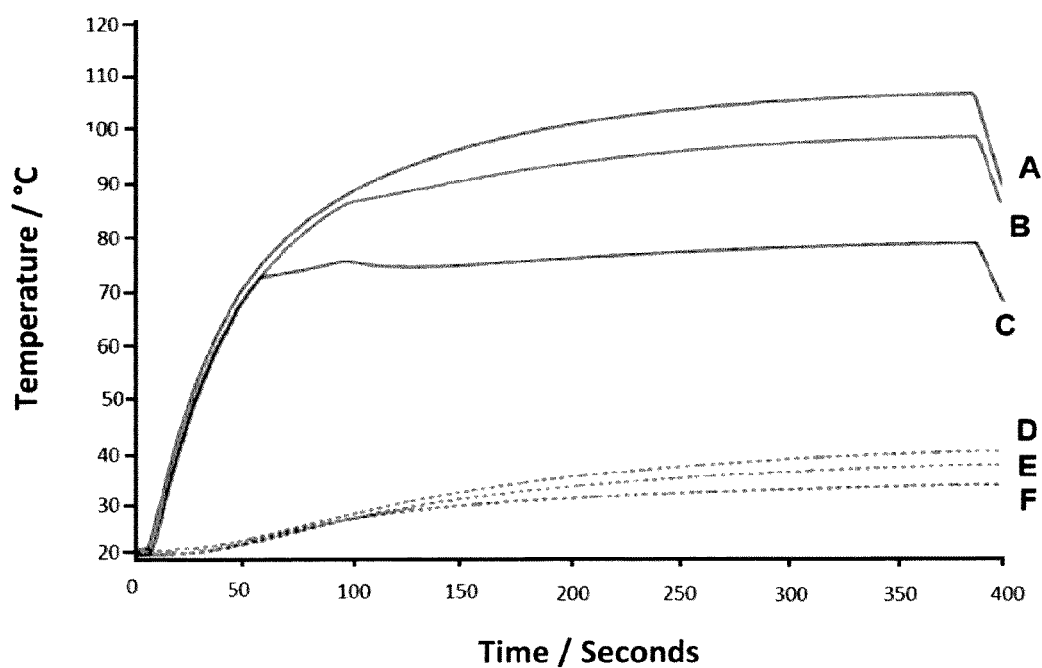

FIG. 3 shows the set, A, B and C, of temperature profiles corresponding to the power profiles A, B and C shown in FIG. 2, and were conducted at an ambient temperature of 22 degrees C. and 50% relative humidity. FIG. 3 also shows the set of temperature profiles of the second compartment for each of the power profiles, profile A corresponds to temperature profile D, profile B corresponds to temperature profile E, and profile C corresponds to temperature profile E. As can be seen, the temperature of the second compartment is substantially the same for each of the power profiles due to the insulating portion 121 of the aerosol-generating article.

The first power profile, A, corresponds to an average nicotine delivery of approximately 150 micrograms per puff; averaged over a group of 12 puffs. The first power profile, B, corresponds to an average nicotine delivery of approximately 100 micrograms per puff; averaged over a group of 12 puffs. The first power profile, C, corresponds to an average nicotine delivery of approximately 50 micrograms per puff; averaged over a group of 12 puffs.

It has been found that reducing the average quantity of nicotine provided in each puff increases the number of usage experiences available to the user.

The invention claimed is:

1. An aerosol-generating system, comprising:
   an aerosol-generating device in cooperation with an aerosol-generating article;
   the aerosol-generating article comprising:
      a first compartment comprising a volatile liquid, and
      a second compartment comprising a delivery enhancing compound,
         wherein the delivery enhancing compound reacts with the volatile liquid in a vapour phase to form an aerosol to be inhaled by a user; and
   the aerosol-generating device comprising:
      an outer housing configured to receive the aerosol-generating article,
      a power supply,
      at least one heater, configured to receive power from the power supply and arranged to heat the first compartment when the aerosol-generating article is received in the outer housing,
      at least one further heater configured to receive power from the power supply and to heat the second compartment when the aerosol-generating article is received in the outer housing,
      an input, configured to receive a plurality of discrete inputs from the user, each discrete input corresponding to a respective discrete quantity of aerosolised volatile liquid required by the user, and
      a controller, configured to:

control an amount of power supplied to the at least one heater by changing a duty cycle, each discrete input of said plurality from the user corresponding to a respective discrete duty cycle among a plurality of discrete duty cycles, such that the discrete quantity of aerosolised volatile liquid is determined by the user input, and control an amount of power supplied to the at least one further heater by changing the duty cycle, wherein the duty cycle for the amount of power supplied to the at least one heater is different than the duty cycle for the amount of power supplied to the at least one further heater, such that vapour concentrations of a quantity of aerosolised delivery enhancing compound and the discrete quantity of aerosolised volatile liquid have a reaction stoichiometry that is balanced proportionally for said each discrete input.

2. The aerosol-generating system according to claim 1, wherein the discrete duty cycles include: between about 90% and about 100%, between about 80% and about 90%, and between about 55% and about 65%.

3. The aerosol-generating system according to claim 1, wherein said each discrete duty cycle of said plurality is a steady-state portion of a respective discrete power profile among a plurality of discrete power profiles.

4. The aerosol-generating system according to claim 3, wherein each discrete power profile of said plurality comprises plural discrete duty cycles among said plurality of discrete duty cycles, including the steady-state portion.

5. The aerosol-generating system according to claim 4, wherein the plural discrete duty cycles include a first duty cycle of between about 90% and about 100%.

6. The aerosol-generating system according to claim 5, wherein at least one of the plurality of discrete power profiles comprises a second duty cycle of between about 65% and about 75%.

7. The aerosol-generating system according to claim 1, wherein the quantity of volatile liquid aerosolised is dependent on a temperature of the first compartment, the temperature of the first compartment being directly related to the amount of power supplied to the at least one heater.

8. The aerosol-generating system according to claim 1, the aerosol-generating article further comprising an insulating element between the first compartment and the second compartment.

9. The aerosol-generating system according to claim 1, further comprising at least one air inlet upstream of the first compartment, and at least one air outlet downstream of the second compartment, the at least one air inlet and the at least one air outlet being arranged to define an air flow pathway extending from the at least one air inlet to the at least one air outlet via the first compartment, and via the second compartment.

10. The aerosol-generating system according to claim 1, wherein the volatile liquid comprises nicotine, and the quantity of nicotine aerosolised per puff of the user on the aerosol-generating device is controllable between about 50 micrograms and about 150 micrograms.

11. The aerosol-generating system according to claim 1, wherein the delivery enhancing compound comprises an acid.

12. An aerosol-generating device for an aerosol-generating system, comprising:
    an outer housing, configured to receive an aerosol-generating article comprising a first compartment comprising a volatile liquid, and a second compartment comprising a delivery enhancing compound, wherein the delivery enhancing compound reacts with the volatile liquid in a vapour phase to form an aerosol to be inhaled by a user;
    a power supply;
    at least one heater, configured to receive power from the power supply and arranged to heat the first compartment when the aerosol-generating article is received in the outer housing;
    at least one further heater configured to receive power from the power supply and to heat the second compartment when the aerosol-generating article is received in the outer housing;
    an input, configured to receive a plurality of discrete inputs from the user, each discrete input corresponding to a respective discrete quantity of aerosolised volatile liquid required by the user; and
    a controller, configured to:
        control an amount of power supplied to the at least one heater by changing a duty cycle, each discrete input of said plurality from the user corresponding to a respective discrete duty cycle among a plurality of discrete duty cycles, such that the discrete quantity of aerosolised volatile liquid is determined by the user input, and
        control an amount of power supplied to the at least one further heater by changing the duty cycle,
    wherein the duty cycle for the amount of power supplied to the at least one heater is different than the duty cycle for the amount of power supplied to the at least one further heater, such that vapour concentrations of a quantity of aerosolised delivery enhancing compound and the discrete quantity of aerosolised volatile liquid have a reaction stoichiometry that is balanced proportionally for said each discrete input.

* * * * *